United States Patent [19]

Hiroi et al.

[11] Patent Number: 4,641,527
[45] Date of Patent: Feb. 10, 1987

[54] INSPECTION METHOD AND APPARATUS FOR JOINT JUNCTION STATES

[75] Inventors: Takashi Hiroi; Takanori Ninomiya, both of Yokohama; Yasuo Nakagawa, Chigasaki, all of Japan

[73] Assignee: Hitachi, Ltd., Tokyo, Japan

[21] Appl. No.: 707,501

[22] Filed: Mar., 1985

[30] Foreign Application Priority Data

Jun. 4, 1984 [JP] Japan .................. 59-112960
Sep. 7, 1984 [JP] Japan .................. 59-186331

[51] Int. Cl.⁴ .......................................... G01N 29/04
[52] U.S. Cl. ........................................ 73/582; 73/588;
 73/643; 73/655; 73/657
[58] Field of Search ................ 73/582, 588, 643, 655,
 73/657

[56] References Cited

U.S. PATENT DOCUMENTS

| 2,728,220 | 12/1955 | Willner | 73/655 |
| 3,645,129 | 2/1972 | Grant | 73/582 |
| 3,952,583 | 4/1976 | Rosati | 73/655 |
| 4,046,477 | 9/1977 | Kaule | 73/643 |
| 4,121,470 | 10/1978 | Kaule | 73/643 |
| 4,218,922 | 8/1980 | Ensminger | 73/588 |
| 4,287,766 | 9/1981 | Ensminger | 73/582 |
| 4,484,820 | 11/1984 | Rosencwaig | 73/643 |

Primary Examiner—Howard A. Brimiel
Attorney, Agent, or Firm—Antonelli, Terry & Wands

[57] ABSTRACT

An object to be inspected which is jointed to a circuit board is vibrated in a contactless manner by applying a gas jet or a magnetic force to the object, a laser beam is irradiated on the object, and a laser beam reflected from the object is detected by a linear sensor to observe a laser speckle pattern for the object. Quality of a joint junction state of the object is judged from the laser speckle pattern.

18 Claims, 27 Drawing Figures

INSPECTION METHOD AND APPARATUS FOR JOINT JUNCTION STATES

BACKGROUND OF THE INVENTION

1. Field of the Invention

This invention relates to an inspection method and apparatus for joint junction states directed to inspect whether soldering is achieved steadily at soldered portions where electrical parts of a large scale integrated (LSI) circuit are soldered to a circuit board.

2. Description of the Prior Art

Defective soldering in electical products leads directly to defective products and must not be permitted absolutely.

Especially, in a large scale electronic computer in which a great number of parts are incorporated at high density, the number of soldered portions increases drastically and all of the joint portions must be inspected for the sake of improving reliability of a product.

Since producibility must also be improved simultaneously with the improvement in reliability, it is necessary to efficiently inspect a great number of soldered portions.

For these reasons, there is at present increasing need for automatic inspection of soldered portions.

However, difficulties are encountered in inspecting soldered portions especially of flat package type parts.

For example, where as shown in FIG. 1c a first flat object 3 typically representative of a soldered portion 1 of a flat package type part shown in FIG. 1a or a wire bonding portion 2 of a large scale integrated circuit shown in FIG. 1b is jointed by soldering to a second object 4, difficulties are faced in inspecting quality of a soldered joint at a junction 5.

Specifically, defects at the soldered portion include complete separation of the first and second objects at the junction, an incomplete joint of the first and second objects represented by mere contact with each other, and displacement of the first and second objects at the junction.

In the flat junction as typically exemplified in FIG. 1c, the complete separation and the incomplete joint equivalent to mere contact are apparently observed as a perfect joint in external appearance and it is very difficult to determine that a defect is present at the junction.

Conventionally, two methods to be described below have been available for inspection of soldered portions of flat package parts.

According to a first method, a soldered portion is vibrated at a frequency of 60 Hz to 200 KHz by means of a vibrator which is brought into direct contact with the soldered portion, and an excited vibration of the soldered portion is detected by a vibration sensor so that the presence or absence of defect in soldering is judged on the basis of a detected vibratory status (U.S. Pat. No. 4,218,922).

According to a second method, a soldered portion is vibrated at varying frequencies within a range of from 20 Hz to 1 MHz or from 150 KHz to 650 KHz by means of a vibrator which is brought into direct contact with the soldered portion, and the magnitude of an excited vibration of the soldered portion is detected by a vibration sensor to measure a frequency response of the soldered portion so that the presence or absence of defect in the soldered portion is judged on the basis of the measured frequency response (U.S. Pat. No. 4,287,766).

These methods face however the following problems. More particularly, since in the aforementioned prior art methods the vibrator is brought into direct contact with the soldered portion to vibrate the soldered portion and the excited vibration is detected by the vibration sensor, (1) The vibrator must be accurately brought into contact with every soldered portion and as a result, the inspection speed slows down; and (2) It is difficult to keep constant the contact state between the soldered portion and the vibrator as well as the vibration sensor, and hence reliability tends to be degraded.

Accordingly, the prior art methods connot be adapted for the large scale electronic computer which incorporates a great number of parts at high density and therefore, urgent development of inspection method and apparatus which meet the requisite reliability and producibility has been desired.

SUMMARY OF THE INVENTION

In view of the above, it is an object of this invention to provide an inspection method for joint junction states which can simultaneously meet the requisite reliability and producibility.

Another object of this invention is to provide an inspection apparatus for joint junction states which can put the above inspection method into practice.

Specifically, according to this invention, the soldered portion is indirectly vibrated by a contactless means in contrast to the prior art methods wherein the vibrator is brought into contact with the soldered portion for directly vibrating it, and a laser beam is used, instead of the vibration sensor, to judge the presence or absence of defect at a joint junction of the soldered portion.

Thus, according to an inspection method of this invention, an object to be inspected is indirectly vibrated by contactless means, a laser beam is irradiated on the vibrating object, a laser beam reflected from the vibrating object and passed through an optical system is observed or detected by a linear sensor, and a laser speckle pattern on the object to be inspected is observed to judge the quality of a junction state of the object.

An inspection apparatus practicing the above method comprises vibration means for indirectly vibrating an object to be inspected in a contactless fashion, laser beam irradiation optical means for irradiating a laser beam emitted from a laser light source on the vibrating object through an irradiation optical system and a half mirror, speckle image detection optical means including a focussing optical system operative to focus a laser beam reflected from the vibrating object and a linear sensor operative to detect a laser speckle pattern on the object, and control means including a linear sensor drive circuit, a defect judging unit for judging the laser speckle pattern observed by the linear sensor, a vibration control unit for controlling the vibration means, a laser beam control unit for controlling the emission of the laser beam, and a position control unit for controlling the position of the object to be inspected.

DESCRIPTION OF THE PREFERRED EMBODIMENTS

Prior to describing the preferred embodiments of the invention, a history of achievement of the present invention will first be described.

With a trend of increasing high density assemblage of parts in mind, the present inventors have studied inspection of soldered portions from the standpoint of improving reliability and producibility.

Namely, the present inventors have studied technical tasks that reliability and inspection speeds should be improved by providing a vibration unit which can impart an identical vibratory condition to a soldered portion of respective objects to be inspected, and that reliability and inspection accuracies should be improved by providing a detector which can detect an excited vibration of the soldered portion in a contactless fashion.

Figure 2:
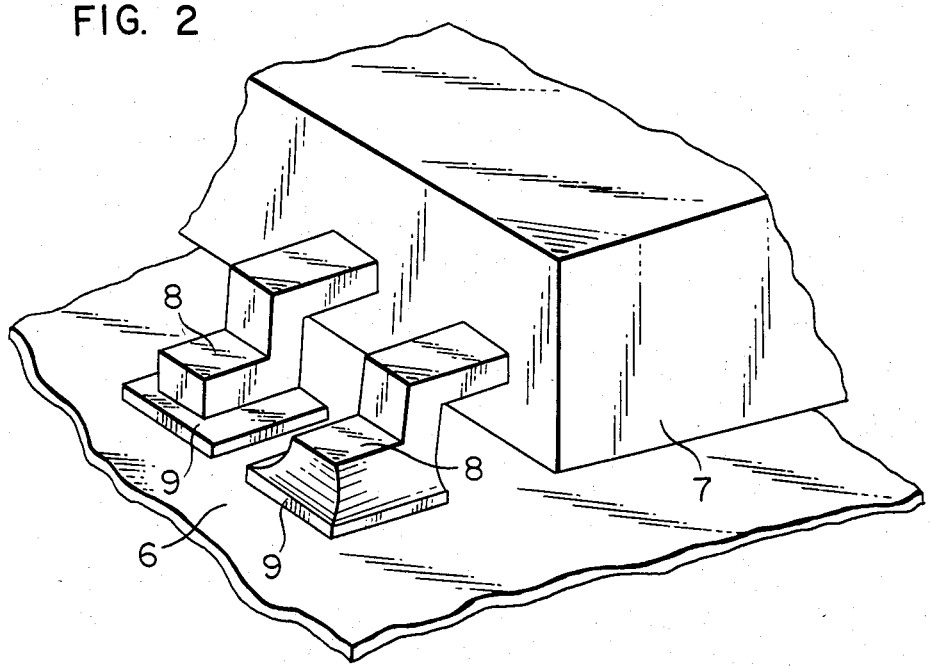
FIG. 2 is a fragmentary perspective view detailing objects to be inspected which are exemplified in the form of soldered portions of flat package type parts.

As a result, in the present invention, a contactless vibration unit is employed which indirectly vibrates a soldered portion. For example, when a lead 8 of a soldered portion of a flat package type part 7 as shown in FIG. 2 is indirectly vibrated under the application of a turbulent air jet or by means of an AC electromagnet, the lead 8 will hardly vibrate if it is securedly fixed to a wiring pattern 9 of a circuit board 6 and hence its joint is acceptable whereas the lead 8 will vibrate intensively if it is disconnected from the wiring pattern of the circuit board and hence its joint is defective. The magnitude of the vibration is therefore measured to judge that a lead undergoing a vibration whose magnitude exceeds a predetermined level is defective in its joint.

In detecting the vibration, a laser beam is irradiated on an object to be inspected to produce a so-called laser speckle pattern of high contrast which can be observed or detected by a sensor. The laser speckle pattern takes place when a laser beam irradiated on the object surface having fine topographical irregularity and taken for a random diffraction grating is diffracted by the diffraction grating and diffracted beams interfere with each other. Since this laser speckle pattern moves as the object moves, a movement of the object can be detected by observing a movement of the laser speckle pattern by means of an optical sensor.

Generally, the optical sensor is classified into a storage type wherein the quantity of incident light is time integrated and then detected and a non-storage type wherein the time-varying quantity of incident light is detected.

Figure 11A:
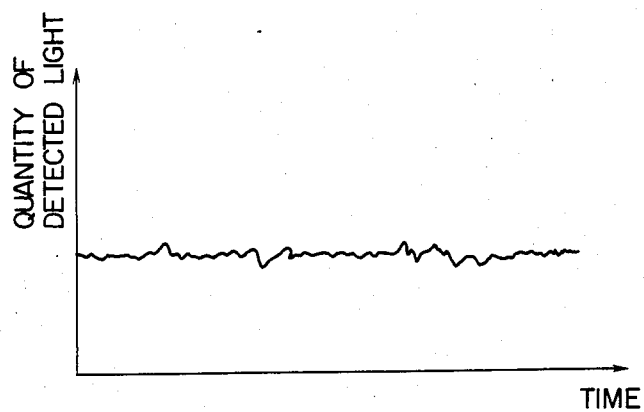
FIG. 11a shows a time varying laser speckle pattern obtained for an acceptable lead joint with the inspection apparatus of the third embodiment.
Figure 11B:
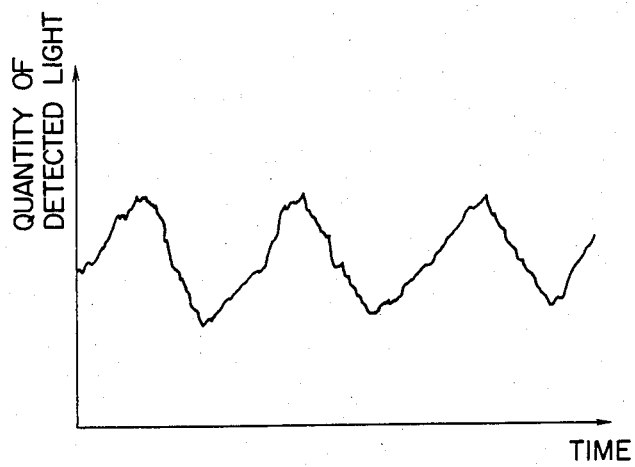
FIG. 11b shows a similar laser speckle pattern obtained for a defective lead joint with the inspection apparatus of the third embodiment.

With a non-storage type sensor, a vibrating laser speckle pattern whose position moves in a vibratory manner is detected to provide a quantity of detection light at one point or location which varies as shown in FIG. 11b, and a stationary laser speckle pattern is detected to provide a quantity of detection light which is substantially constant as shown in FIG. 11a.

Figure 3A:
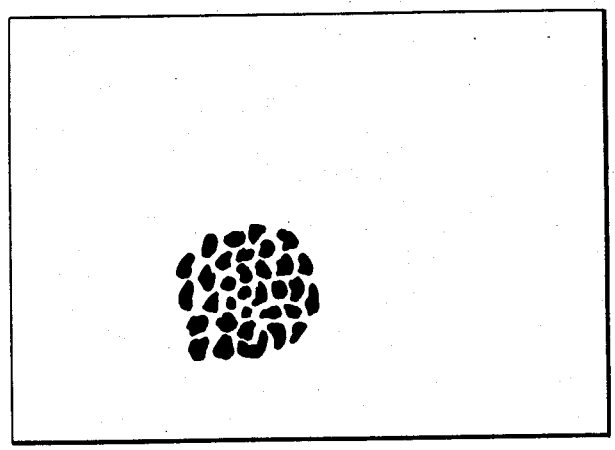
FIG. 3a shows a laser speckle pattern image for an acceptable lead joint.
Figure 3B:
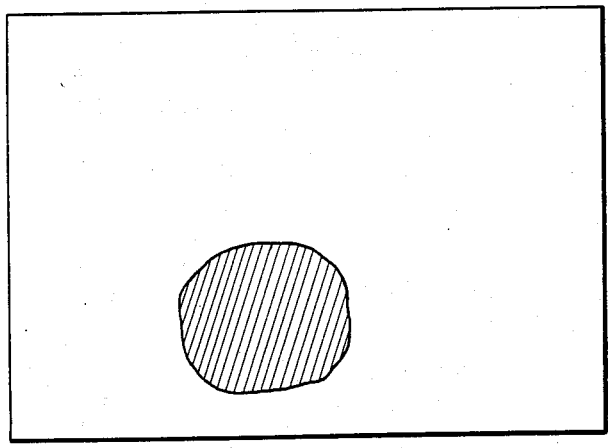
FIG. 3b shows a laser speckle pattern image for a defective lead joint.

With a storage type sensor, a vibrating laser speckle pattern whose position moves in a vibratory manner is detected to provide a quantity of detection light at one point which is substantially constant irrespective of locations if the storage time is set to exceed the period of vibration. Accordingly, for a detection signal distribution corresponding to a stationary laser speckle pattern, a laser speckle pattern image of high contrast as shown in FIG. 3a is observed whereas for a vibrating laser speckle pattern, a faint image without contrast as shown in FIG. 3b is observed.

An inspection apparatus according to a first embodiment of the invention will now be described. An object to be checked for its joint junction state has already been exemplified in FIG. 2, illustrating that the leads 8 of the part 7 of the LSI circuit are to be soldered to the wiring patterns 9 formed on the circuit board 6.

Figure 4:
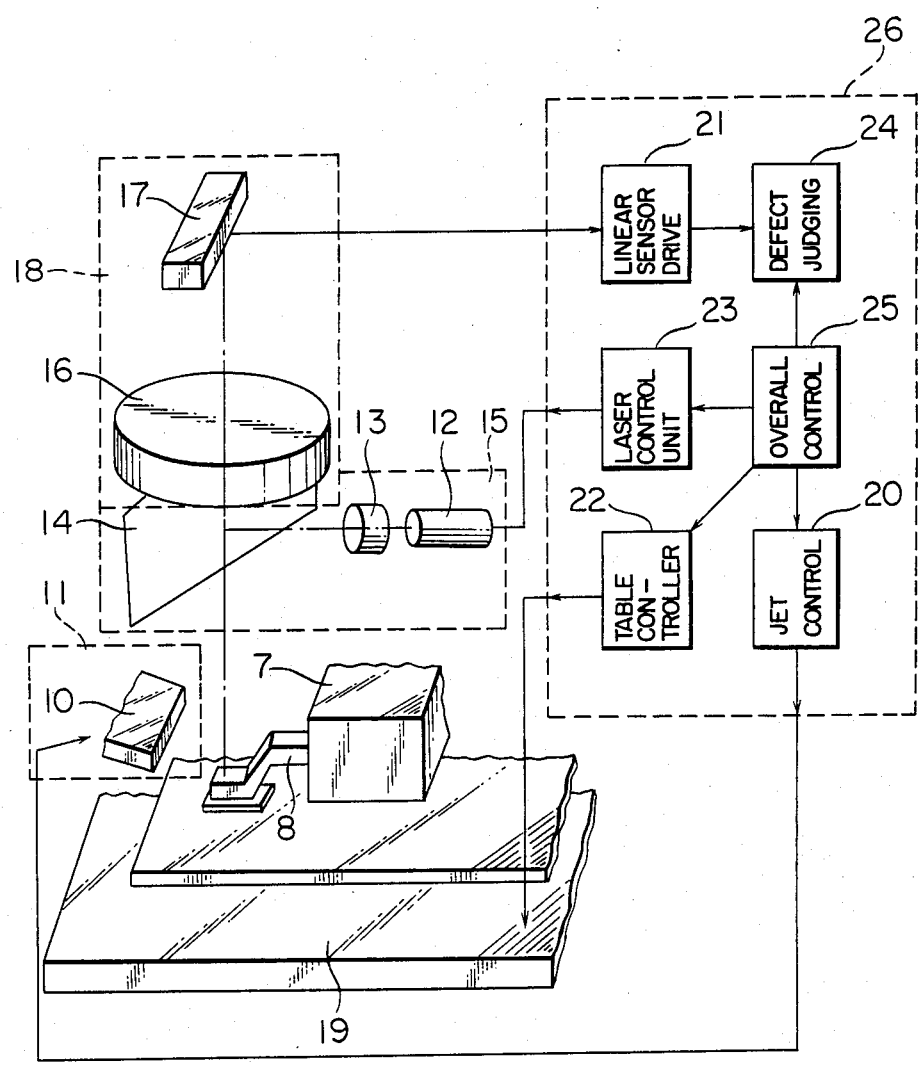
FIG. 4 is a schematic showing an inspection apparatus according to a first embodiment of the invention.

Referring to FIG. 4, an inspection apparatus for judging the presence or absence of a defect at a lead joint for the flat package type part 7 will be described. The inspection apparatus comprises a vibration system 11 utilizing an air nozzle 10 which applies a turbulent air jet to a plurality of soldered portions representing objects to be inspected in order that the soldered portions or leads disconnected from the wiring patterns are vibrated; a laser beam irradiation optical system 15 including a laser 12 emitting a laser beam to be irradiated on a soldered portion, an irradiation optical system 13 and a half mirror 14; a speckle image detection optical system 18 including a focussing optical system 16 having an image plane set on an in-focus position for detection of a laser speckle pattern image or on an out-of-focus position therefor and a storage type linear sensor 17; and a control system 26 including a table controller 22 for controlling an X-Y table 19, a jet control unit 20 for controlling the air jet, a linear sensor drive circuit 21, a laser control circuit 23, a defect judging unit 24, and an overall control unit 25.

Figure 5:
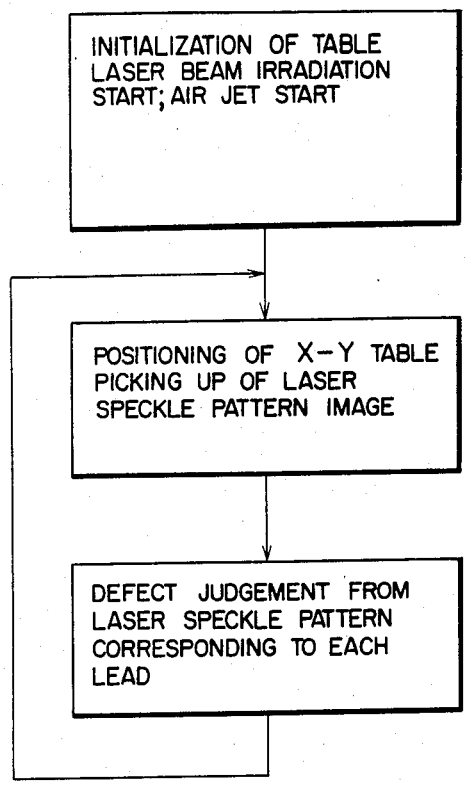
FIG. 5 is a flow chart showing an inspection sequence in the first embodiment.

To generally describe the overall operation for inspection with reference to FIGS. 4 and 5, the X-Y table 19 is first, prior to the inspection, moved to an inspection start position in response to instructions from the overall control unit 25 and table controller 22, a laser beam is irradiated on the top surface of a lead 8 representing an object to be inspected, and the application of an air jet from the air nozzle 10 to a soldered portion of the lead 8 is started.

Figure 6:
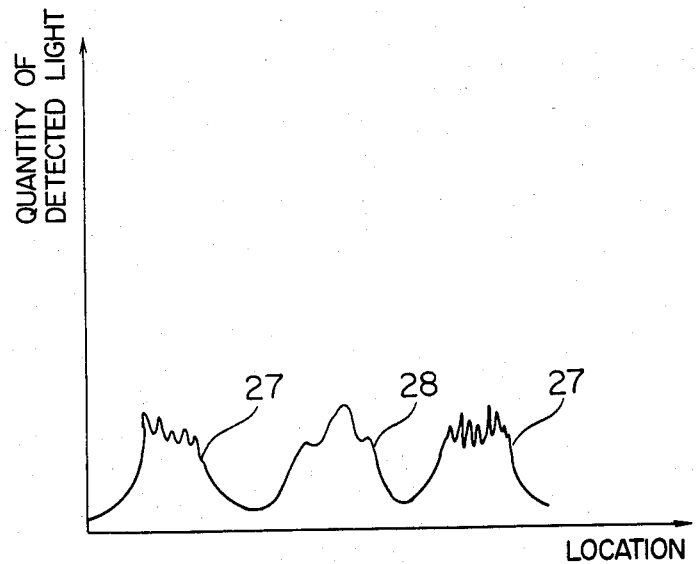
FIG. 6 is a graph showing waveforms corresponding to laser speckle pattern images obtained in accordance with the first embodiment.

Subsequently, the following operation is repeated to inspect individual leads 8. More particularly, the X-Y table 19 is driven to position a particular lead 8 to be inspected of the flat package type part 7 at an inspection position, a laser beam is irradiated on the top surface of the lead, and an air jet is applied to a soldered portion. Under this condition, the particular lead will not vibrate if its joint is acceptable but will vibrate if its joint is defective. This stationary or vibratory state is observed by the storage type linear sensor 17 having a sample rate larger than a vibration frequency, thus providing waveforms corresponding to laser speckle patterns as shown in FIG. 6. The presence or absence of a defective junction state is judged from a waveform representative of a laser speckle pattern obtained at a location corresponding to each lead. In FIG. 6, a waveform 27 represents a laser speckle pattern of an acceptable joint in the first embodiment and a waveform 28 represents a laser speckle pattern of a detective joint in the first embodiment.

In judging the defect, it will be appreciated from FIG. 6 that while a laser specle pattern image observed by the storage type linear sensor 17 for an acceptable lead has a train of steep short-pitch peaks since the lead does not vibrate, a laser speckle pattern image for a defective lead joint takes a large-pitch smooth form since a vibrating laser speckle pattern due to vibration of the lead is integrated for detection. Based on this difference, the number of locations (peaks) where the quantity of light of a laser speckle pattern image for each lead which amounts to maximum levels is measured and compared with a predetermined threshold number. A lead joint providing a laser speckle pattern image having the number of peaks which is less than the threshold number is judged to be defective.

This manner of judgement may be modified as follows:

(i) An average of pitches between adjacent maximum levels of the quantity of light of a laser speckle pattern image (distance between adjacent peaks) is computed and the quality is judged from whether the average is larger than a predetermined threshold value or not; and (ii) absolute values of the differentiated quantities of eight of laser speckle pattern images are averaged and the quality is judged from whether the average is larger than a predetermined threshold value or not.

According to the first embodiment, the following effects can be attained:

(i) Since the lead is indirectly vibrated under the application of a turbulent air jet, the vibration conditions for all of the soldered portions can be uniform to thereby improve reliability. In addition, when the vibration is effected at frequencies within a wide range inclusive of a natural frequency of a defective-joint lead, the lead can be vibrated to a large amplitude;

(ii) Thanks to the use of the storage type sensor, a small amplitude signal can be picked up and even with a laser of a small output, a laser speckle pattern image sufficient to be detected can be obtained; and (iii) The manner of judgement is so simplified as to increase the inspection speed and to simplify the apparatus.

Figure 7:
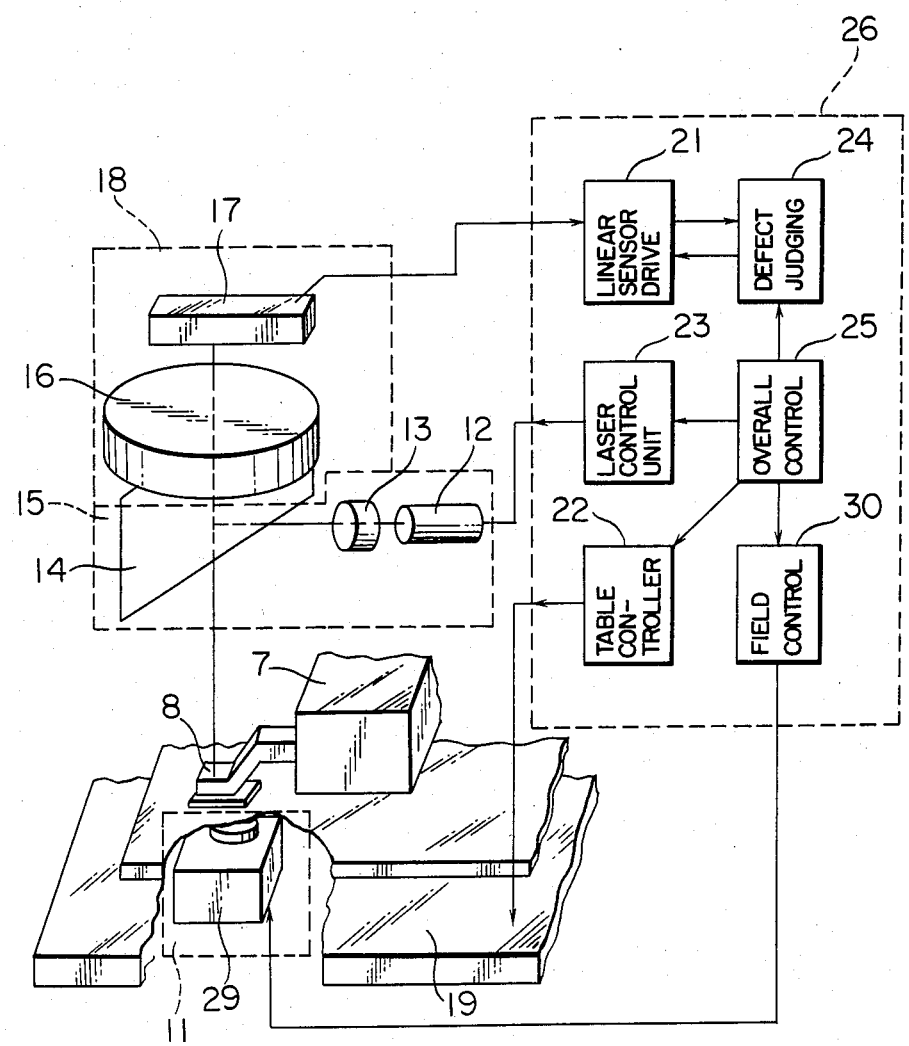
FIG. 7 is a schematic showing an inspection apparatus according to a second embodiment of the invention.

FIG. 7 illustrates an inspection apparatus according to a second embodiment of the invention directed to inspection of a similar object to that of the first embodiment. The inspection apparatus comprises a vibration system 11 utilizing an AC electromagnet 29 for vibrating a lead 8 of part 7 made of a ferromagnetic material such as iron; a laser beam irradiation optical system 15 including a laser 12 emitting a laser beam to be irradiated on a soldered portion, an irradiation optical system 13 and a half mirror 14; a speckle image detection optical system 18 including a focussing optical system 16 and a storage type linear sensor 17 for detection of a laser speckle pattern image; and a control system 26 including a table controller 22 for controlling a positioning X-Y table 19, a field control unit 30 for controlling the AC electromagnet 29, a sensor drive circuit 21 for picking up a sensor signal, a laser control circuit 23, a detect judging unit 24, and an overall control unit 25.

Figure 8:
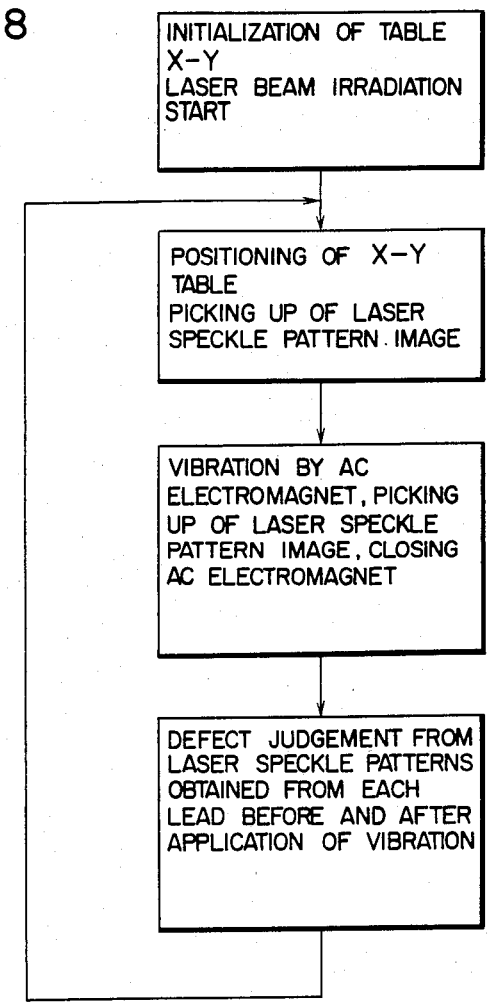
FIG. 8 is a flow chart showing an inspection sequence in the second embodiment.

To generally describe the overall operation for inspection with reference to FIGS. 7 and 8, the X-Y table 19 is first, prior to the inspection, moved to an inspection start position is response to instructions from the overall control unit 25 and table controller 22, and the irradiation of a laser beam on the top surface of a lead representing an object to be inspected is started.

Figure 9:
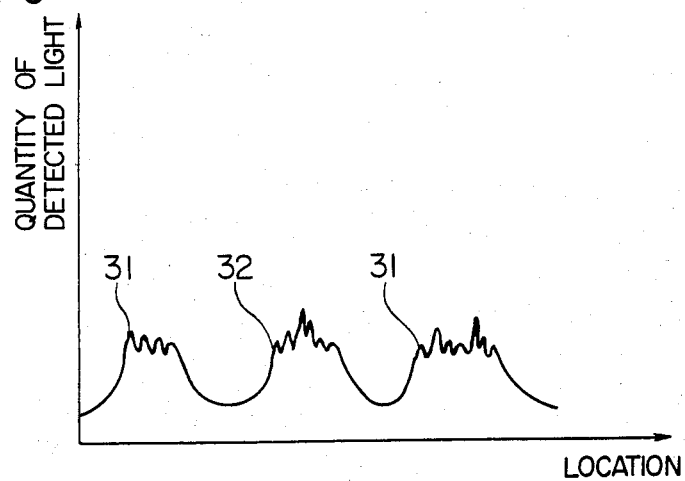
FIG. 9 is a graphical representation showing waveforms corresponding to laser speckle pattern images in the second embodiment obtained prior to vibrating objects to be inspected.

Subsequently, the following operation is repeated to inspect individual soldered portions. More particularly, the X-Y table 19 is driven to position a particular lead 8 to be inspected of the flat package type part 7 at an inspection position, so that a laser speckle pattern as shown in FIG. 9 is obtained. In the figure, a waveform 31 represents a laser speckle pattern of an acceptable joint prior to vibration in the second embodiment and a waveform 32 represents a laser speckle pattern of a defective lead joint prior to vibration in the second embodiment. Under this condition, since all of the laser speckle patterns are stationary, the pattern images for all of the leads are substantially identical. Subsequently, a vibration is applied to the part lead 8 by means of the AC electromagnet 29 so that the lead will not vibrate if its joint is acceptable but it will vibrate if its joint is defective. Under the application of the vibration, laser speckle pattern images as represented by waveforms shown in FIG. 6 can be obtained. Laser speckle patterns obtained at a location corresponding to each lead before and after the vibration are compared to judge the presence or absence of defect.

In judging the defect, it will be appreciated that laser speckle pattern images obtained from the storage type linear sensor 17 are of substantially identical forms as shown in FIG. 9 for all the leads before the vibration applied but take waveforms as shown in FIG. 6 resembling those obtained in the first embodiment after the application of the vibration. Based on this difference, quantities of light of laser speckle pattern images corresponding to each lead obtained before and after the application of the vibration are differentiated with respect to a location, differentiated values are converted into binary values wherein a positive differential is "1" and a negative differential is "0", and binary differentials obtained before and after the application of the vibration are correlated for comparison so that a defective junction state is determined by a correlation coefficient which is less than a predetermined threshold value.

This manner of judgement may be modified as follows:

(i) A ratio or difference between averaged pitches between adjacent maximum levels of the quantities of light of the laser speckle pattern images obtained before and after the vibration applied is computed and the defective junction state is determined by a computed value which exceeds a predetermined threshold value;

(ii) A ratio or difference between the numbers of maximum levels of the quantities of light of the laser speckle pattern images obtained before and after the vibration applied is measured and the defective junction state is determined by a measured value which is less than a predetermined threshold value;

(iii) The quantities of light of the laser speckle pattern images obtained before and after the vibration applied are subjected to a high speed Fourier transform, a ratio or difference between frequencies which take maximum values within a frequency range is computed, and the defective junction state is determined by a computed value which is less than a predetermined threshold value; and (iv) A ratio or difference between averaged absolute values of differentials of the quantities of light of the laser speckle pattern images obtained before and after the application of the vibration is computed and the defective junction state is determined by a computed value which is less than a predetermined threshold value.

Effects attained by the second embodiment are as follows:

(i) Thanks to the indirect vibration by the electromagnet, a stable vibration can be effected in a contactless fashion; and (ii) Because of comparison between the laser speckle pattern images obtained before and after the application of the vibration, reliability can be improved.

Figure 10:
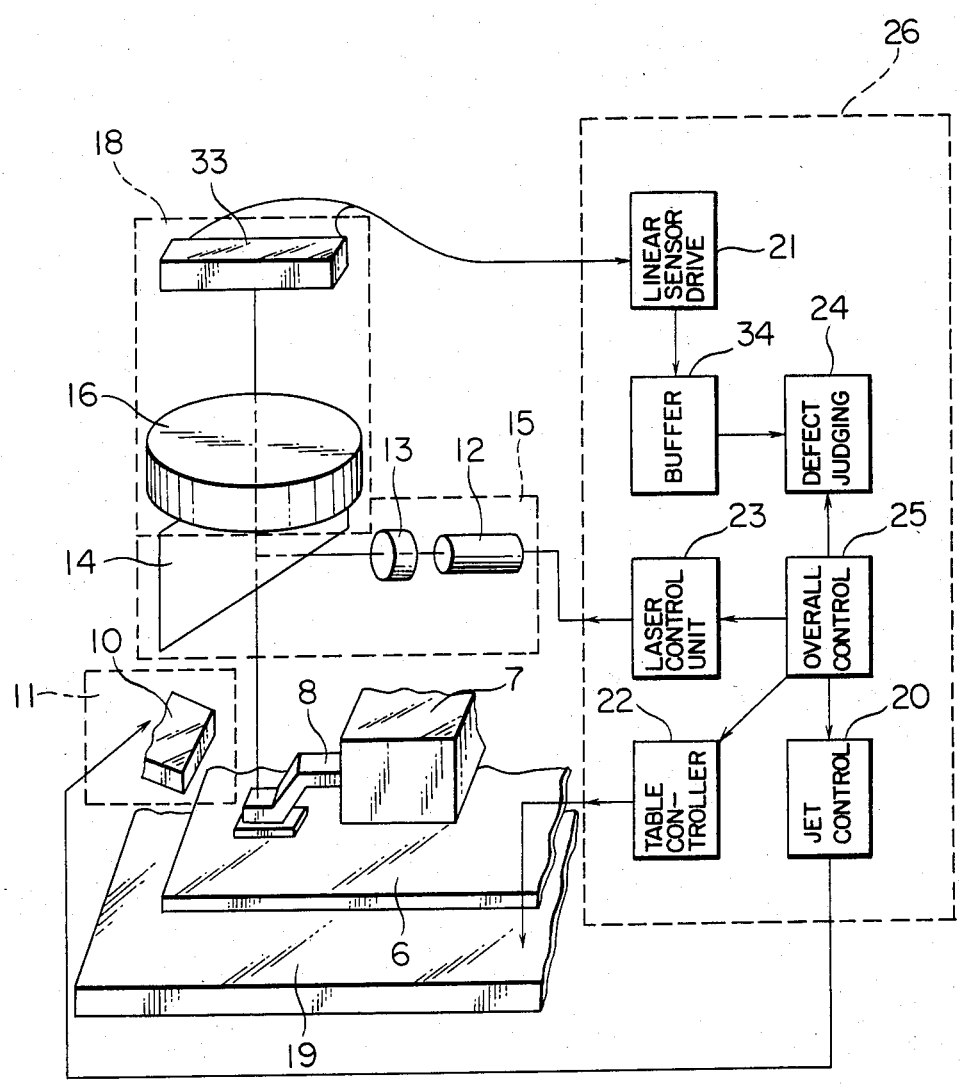
FIG. 10 is a schematic showing an inspection apparatus according to a third embodiment of the invention.

FIG. 10 illustrates an inspection apparatus according to a third embodiment of the invention directed to inspection of a similar object to that of the first and second embodiments. The inspection apparatus comprises a vibration system 11 utilizing an air nozzle 10 which applies a turbulent air jet at a vibratory flow rate to a plurality of soldered portions to be inspected simultaneously in order that soldered portions or leads of defective joint are vibrated; a laser beam irradiation optical system 15 including a laser 12 emitting a laser beam to be irradiated on a soldered portion, an irradiation optical system 13 and a half mirror 14; a speckle image detection optical system 18 including a focussing optical system 16 having an image plane set on an in-focus position for detection of a laser speckle pattern impage or on an out-of-focus position therefor and a non-storage type linear sensor 33 which produces parallel outputs; and a control system 26 including a table controller 22 for controlling an X-Y table 19 operative to position the object to be inspected, a jet control unit 20 for controlling the flow rate of the air jet, a sensor drive circuit 21, a buffer 34 for storing parallel output signals, a laser control circuit 23, a defect judging circuit 24, and an overall control unit 25.

To generally describe the overall operation for inspection with reference to FIG. 10 and FIG. 5 referred to previously, the X-Y table 19 is first, prior to the inspection, moved to an inspection start position in response to instructions from the overall control unit 25 and table controller 22, and the irradiation of a laser beam on the top surface of a lead is initiated. Subsequently, the following operation is repeated to inspect individual soldered portions. More particularly, the X-Y table 19 is driven to position a particular lead 8 to be inspected of a flat package type part 7 at an inspection position, and an air jet is then applied from the air nozzle 10 to a soldered portion. Under this condition, the particular lead will not vibrate if its joint is acceptable but will vibrate if its joint is defective. This state is observed by the non-storage type parallel output linear sensor 33 to provide a time varying waveform corresponding to a laser speckle pattern image as shown in FIG. 11a or 11b. A time varying laser speckle pattern image form obtained at a location corresponding to each lead is stored in the buffer 34 and the defect is judged from a stored time varying form.

Figure 12A:
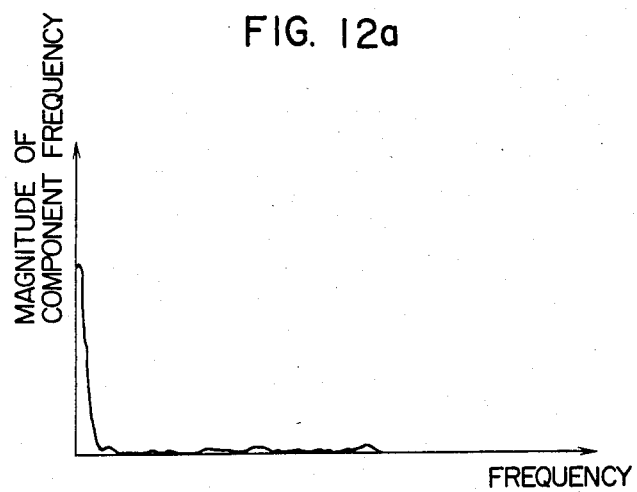
FIGS. 12a and 12b show frequency responses respectively obtained from analysis of the pattern outputs of FIGS. 11a and 11b by means of a spectrum analyzer.
Figure 12B:
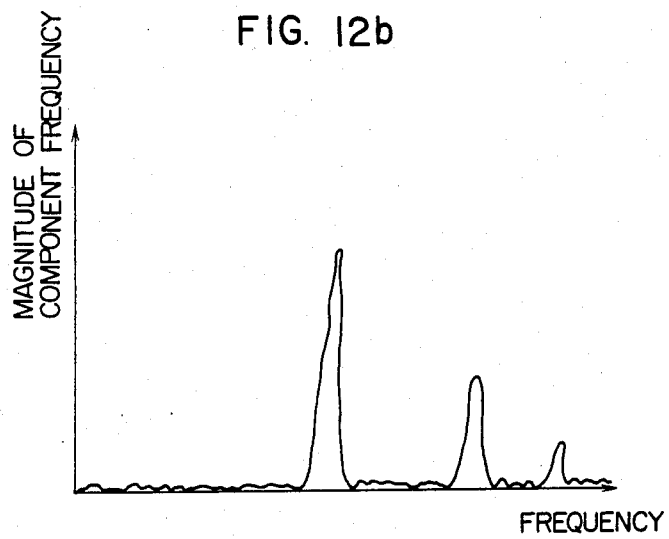

In judging the defect, it will be appreciated that while the quantity of light of the laser speckle pattern image observed by the non-storage type parallel output linear sensor will not substantially vary as shown in FIG. 11a if the part lead has an acceptable joint and does not vibrate, the quantity of light will vibrate as shown in FIG. 11b if the part lead has a defective joint and vibrates at its natural frequency. By analyzing the time varying laser speckle pattern image waveforms by means of a spectrum analyzer, frequency response characteristics as shown in FIGS. 12a and 12b can be obtained. The defective joint is determined by a peak frequency within the frequency range which exceeds a predetermined threshold value as shown in FIG. 12b.

This manner of judgement may be modified as follows:

(i) The time varying laser speckle pattern image form is converted into a floating binary value and the number of changes of from "0" to "1" or from "1" to "0" is computed. The defective joint is determined by a computed value which exceeds a predetermined threshold value; and (ii) As in item (i) above, the time varying laser speckle pattern image form is converted into a floating binary value and pitches between adjacent changes of from "0" to "1" or from "1" to "0" are averaged, and the defective joint is determined by an average value which is less than a predetermined threshold value.

The sensor used in the third embodiment may be replaced with the following alternative ones:

(i) A sensor using an image detector which can be subjected to random scanning. With this sensor, the respective leads are scanned sequentially while detecting time varying quantities of incident light; and (ii) A point sensor such as a photomultiplier and with this sensor, the inspection is carried out by driving the X-Y table in respect of each lead in a step-and-repeat fashion.

According to the third embodiment, the following effects can be attained:

(i) Since the time varying laser speckle pattern image is measured, the vibration frequency of the lead can be recognized to provide large amounts of information, thereby ensuring highly reliable judgement which never misses defective junction states; and (ii) The lead is vibrated by a turbulent air jet as applied thereto at a vibratory flow rate. Consequently, even when a soldered joint portion abuts against a defective joint lead to prevent the defective lead from vibrating at its natural frequency, this lead can be vibrated at a frequency of the vibratory flow rate and the defective joint can be detected.

Figure 13:
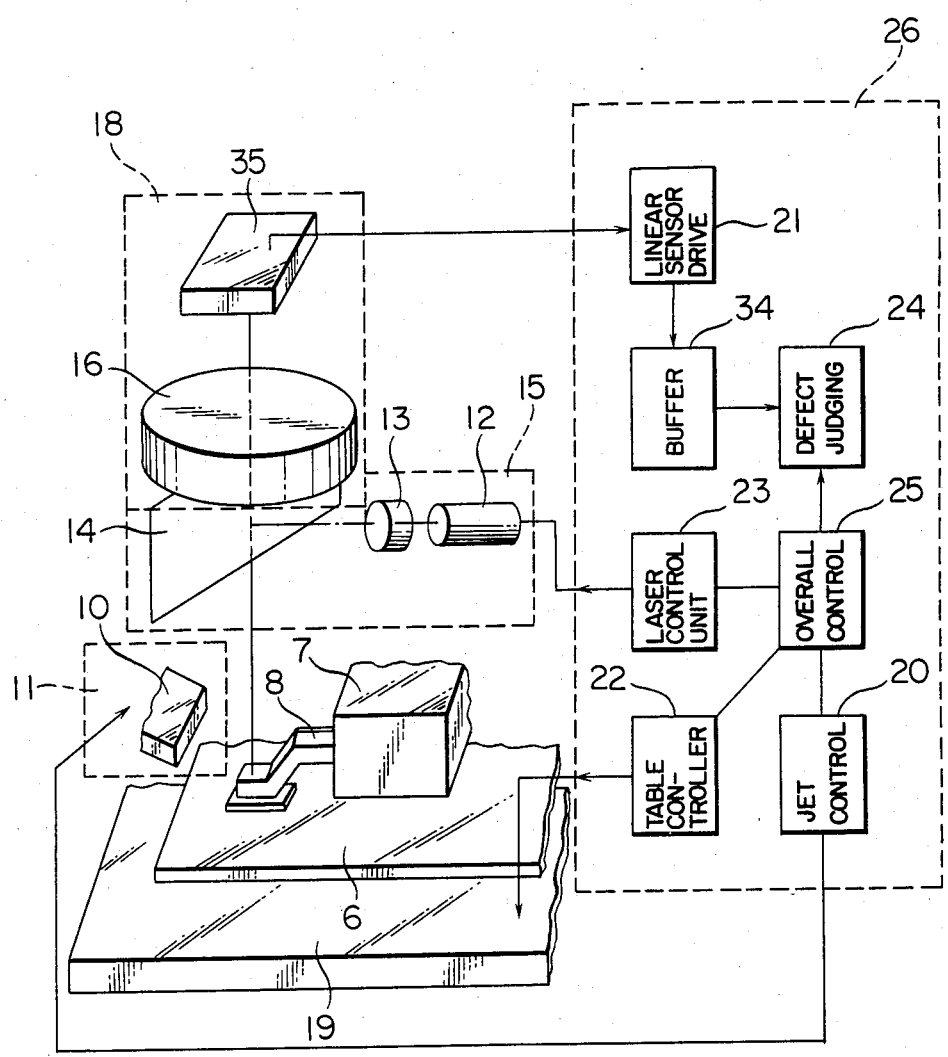
FIG. 13 is a schematic showing an inspection apparatus according to a fourth embodiment of the invention.

FIG. 13 illustrates an inspection apparatus according to a fourth embodiment of the invention directed to inspection of a similar object to that of the first to third embodiments.

The inspection apparatus comprises a vibration system 11 utilizing an air nozzle 10 which applies a turbulent air jet to an object to be inspected; a laser beam irradiation optical system 15 including a laser 12, an irradiation optical system 13 and a half mirror 14; a speckle image detection optical system 18 including a focussing optical system 16 and a storage type two-dimensional sensor 35; and a control system 26 including a table controller 22 for controlling an X-Y table 19, a jet control unit 20, a sensor drive circuit 21, a buffer 34 for storing two-dimensional signals, a laser control circuit 23, a defect judging unit 24, and an overall control unit 25.

Figure 14:
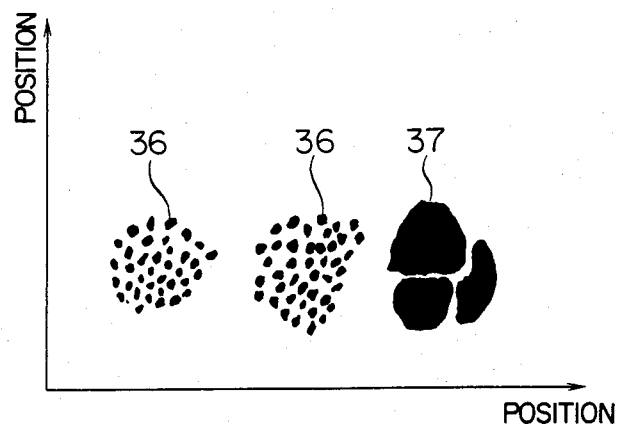
FIG. 14 shows two-dimensional laser speckle pattern images detected in the fourth embodiment of the invention.

To generally describe the overall operation for inspection with reference to FIG. 13 and FIG. 5 referred to previously, the X-Y table 19 is first, prior to the inspection, moved to an inspection start position in response to instructions from the overall control unit 25 and table controller 22, and the irradiation of a laser beam on the top surface of a lead is initiated. Subsequently, the following operation is repeated to inspect individual soldered portions. More particularly, the X-Y table 19 is driven to position a particular lead 8 to be inspected of a flat package type part 7 at an inspection position, and the application of an air jet from the air nozzle 10 to the soldered portion is initiated. This condition is observed by the storage type two-dimensional sensor 35 to provide a two-dimensional image of a laser speckle pattern as shown in FIG. 14. A distribution of a two-dimensional laser speckle pattern image obtained at a location corresponding to each lead is stored in the buffer 34. The defect is judged from time variation of the stored two-dimensional pattern image.

In judging the defect, it will be appreciated that while the laser speckle pattern image observed by the storage type two-dimensional sensor will be a clear speckle pattern image 36 shown in FIG. 14 if the part lead has an acceptable joint and does not vibrate, the observed speckle pattern image will be a faint speckle image 37 if the part lead has a defective joint and hence vibrates. This laser speckle pattern image is subjected to a two-dimensional high speed Fourier transform, and for judgement of detect, a peak position within the frequency range is compared with a predetermined position for an acceptable sample.

This manner of judgement may be modified as follows:

(i) The two-dimensional laser speckle pattern image is converted into a floating binary value, and areas of respective bright regions are computed and averaged. The defective junction state is determined by an average value which exceeds a predetermined threshold value; and (ii) The two-dimensional laser speckle pattern image is applied with the Laplace transformation operator to detect a peak brightness position, and the number of peak positions per unit area is computed. The defective junction state is determined by a computed value which is less than a predetermined threshold value.

Effects attained by the fourth embodiment are as follows:

(i) Because of obtainment of the two-dimensional image, information can be obtained from a wide region and a highly reliable inspection can be ensured;

(ii) Even for a lead positioned with poor accuracies, the inspection can be carried out; and (iii) Thanks to the vibration by the air jet, the amplitude of the vibration can be extended as in the first embodiment.

Figure 15:
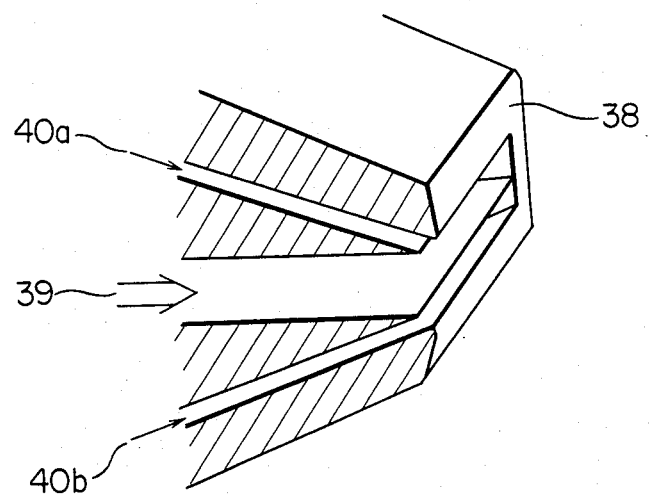
FIG. 15 is a fragmentary sectional perspective view showing an inproved nozzle whose jet direction is controllable.

Although not described in connection with the four embodiment set forth so far, the direction of the jet can be changed in a vibratory fashion and a resultant turbulent jet directed to different directions can be applied for vibrating the lead. More specifically, in a nozzle 38 as shown in FIG. 15, control flows 40a and 40b which are 180° out of phase with respect to a main jet 39 are added thereto in order that the direction of the main jet can be changed vertically in a vibratory fashion, thereby obtaining the same effect as that of the air jet whose flow rate is vibrated.

In the inspection apparatus according to the foregoing embodiments of the invention, various types of vibration application, vibration detection and defect judgement have been employed which are summarized below.

(1) Vibration application
(i) Injection of an air jet utilizing only a turbulent flow.
(ii) Injection of an air jet added with a vibratory flow rate.
(iii) Injection of an air jet the direction of which is vibrated.

(2) Vibration detection
(i) Detection of a time varying pattern image or waveform.
(ii) Detection by a storage type linner sensor having a storage time which is larger than a period of natural vibraion of a lead to be inspected.
(iii) Detection by a storage type two-dimensional sensor having a storage time which is larger than a period of natural vibration of a lead to be inspected.

(3) Defect judgement
(i) Judgement based on only a vibratory state of a laser speckle pattern obtained when a lead is applied with a vibration.
(ii) Judgement based on comparison of vibratory states of laser speckle patterns obtained before and after a lead is applied with a vibration.

In the foregoing embodiments, typical combinations of the aforementioned types have been described. It should however be understood that any types can be combined for the inspection in 18 ways.

Figure 1A:
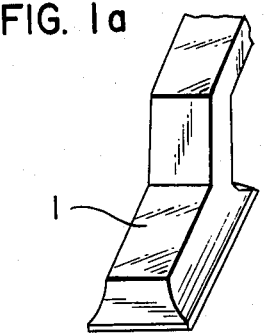
FIGS. 1a to 1c illustrate objects to be inspected according to the invention, with FIG. 1a showing a soldered portion of a flat package type part, FIG. 1b showing a wire bonding portion of an LSI circuit and FIG. 1c showing a general form of an object to be inspected.
Figure 1B:
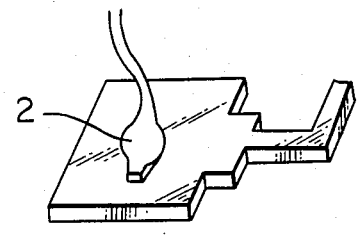
Figure 1C:
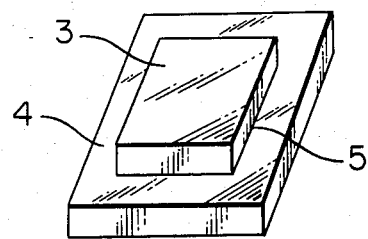

In addition, the object to be inspected is not limited to the soldered portion of the flat package type part but may be extend, as described previously, to the general form shown in FIG. 1c having a similar joint structure.

The laser beam detection optical system 18 may be modified as will be described hereinafter.

Figure 16:
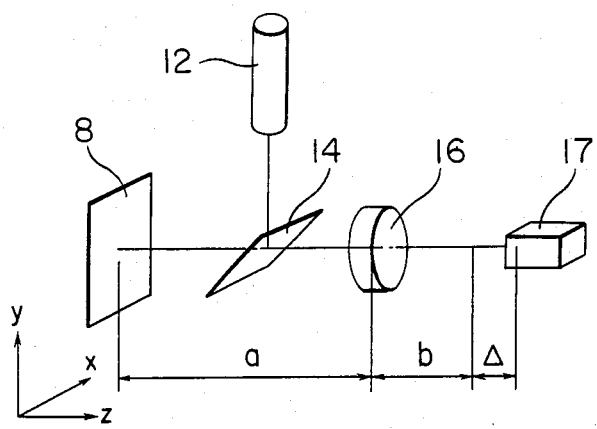
FIG. 16 is a schematic useful in explaining the principle of the invention.

The principle of the laser beam detection employed in the first to fourth embodiments is best seen from FIG. 16. More particularly, a laser beam emitted from a laser light source 12 is irradiated on an object 8 through a half mirror 14, and a laser speckle pattern image generated under the irradiation of the laser beam is focussed by a focussing optical system 16 and observed by an optical sensor 17.

In this optical system, an amount of movement $A_x$ of the laser speckle pattern image in a direction x is indicated by the following equation:

$$A_x = \frac{b + \Delta}{2} a_x - \frac{b}{a} \Delta \cdot \Omega_y \quad (1)$$

where
- a: distance between object and lens,
- b: distance between lens and image formation position,
- $\Delta$: defocussing or out-of-focus amount from image formation position,
- $a_x$: amount of movement of object,
- $\Omega_y$: amount of rotation of object about y axis.

It will be seen from equation (1) that when the sensor 17 is placed on an image formation plane ($\Delta=0$), the amount of movement of the speckle pattern image equals a product of the amount of movement of the object 8 and a magnification. Contrary to this, when the sensor 17 is placed on a defocussing position which is distant by $\Delta$ from the image formation plane, the laser speckle pattern image moves in response to a rotational movement of the object 8 in such a manner that in proportion to an increase in the defocussing amount $\Delta$, a small amount of rotational movement of the object is magnified into a large amount of movement of the laser speckle pattern image. Accordingly, where the object to be inspected is associated with a mechanism which effects a rotational movement, it is very effective to place the sensor 17 on the defocussing position.

The laser speckle pattern image is confined in a small area at the image formation position but extended at the defocussing position. If the objects 8 to be inspected are arrayed at a small pitch the extended laser speckle pattern images generated from the individual objects will mutually overlap and cannot be discriminated.

Figure 17:
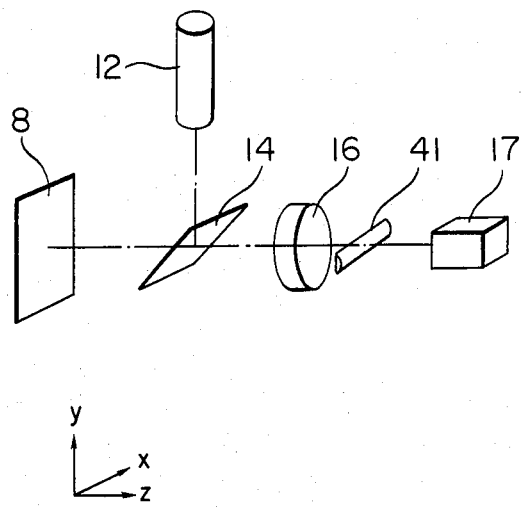
FIG. 17 is a schematic for explaining the principle of an inspection apparatus according to a fifth embodiment of the invention which has an improved speckle image detection optical system.

To cope with this problem, a cylindrical lens 41 is inserted as shown in FIG. 17 between the focussing optical system 16 and the sensor 17 to ensure that the objects are so related to each other as to keep the image formation in the array direction but the defocussing occurs in a direction orthogonal to the array direction. As a result, the laser speckle pattern images generated from the respective objects can be sufficiently separated from each other and the amount of defocussing can be increased, thereby sufficiently raising the vibration detection sensitivity.

By substituting a diffraction grating for the cylindrical lens, a diffraction image can be observed with the defocussing in only one direction maintained.

Figure 18A:
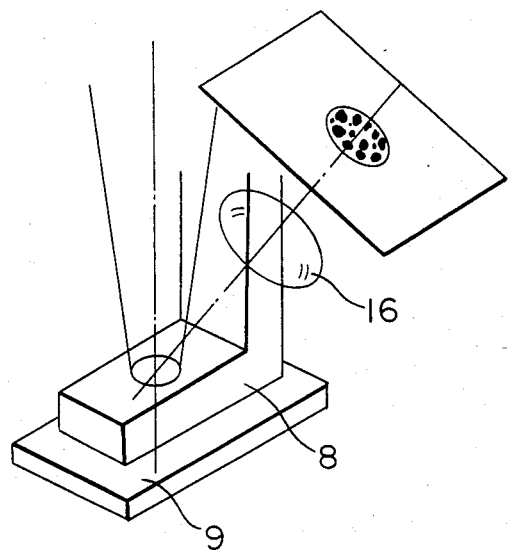
FIGS. 18a and 18b are fragmentary perspective views showing the relation between optical axes of the laser beam irradiation optical system and speckle image detection optical system in an inspection apparatus according to a sixth embodiment of the invention.
Figure 18B:
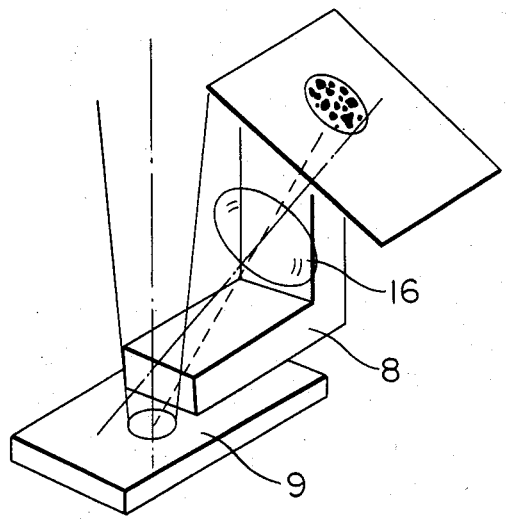

An improved embldiment to be described below intends to prevent missing of defect detection. In this embodiment, the optical axis of a laser beam irradiation optical system is not made parallel to the optical axis of the speckle image detection optical system but the latter optical axis is inclined with respect to the former optical axis so that the laser beam irradiated position can be viewed obliquely. With this construction, a speckle pattern image is formed at a position as shown in FIG. 18a when a laser beam impinges on a correctly positioned lead 8 to be inspected but a speckle pattern image generated from an incorrectly positioned lead is formed at a position as shown in FIG. 18b which is displaced from the position of FIG. 18a. By discriminating and detecting the displacement of the speckle pattern image, missing of the detection of a displacement of the lead can be avoided even when a defective joint and a displacement of the lead take place simultaneously.

Figure 19:
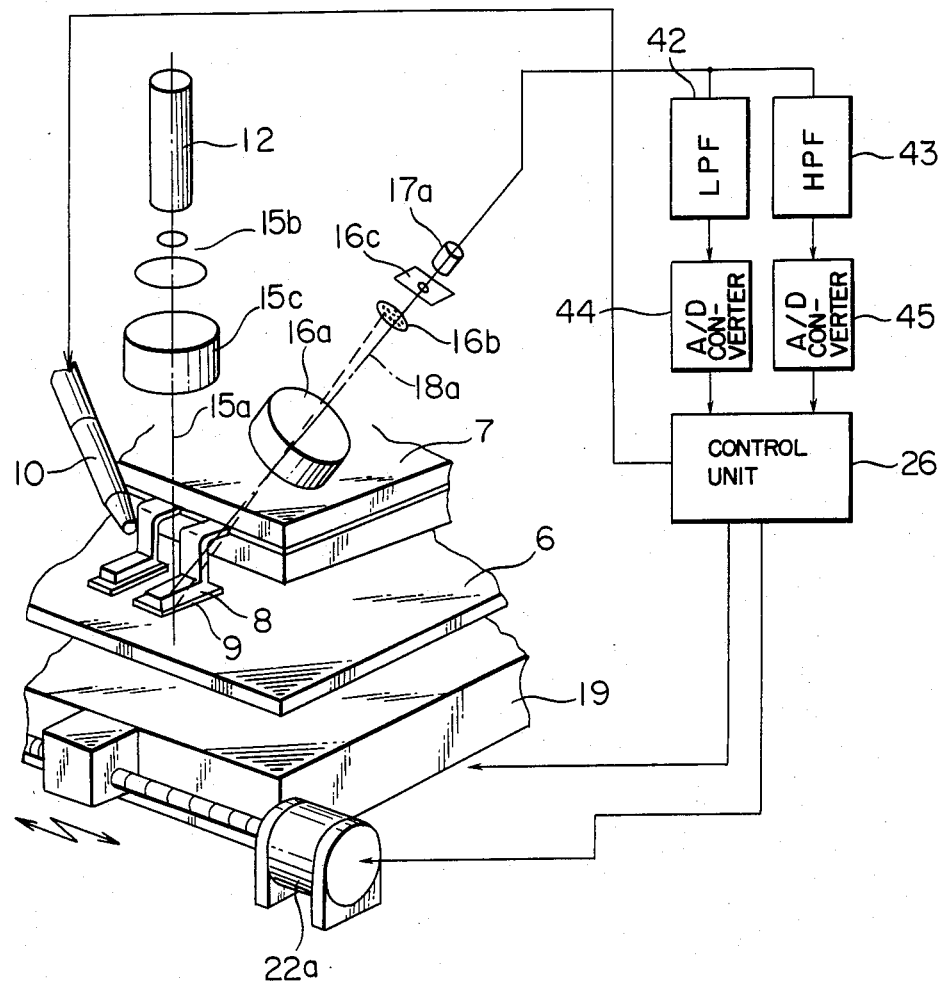
FIG. 19 is a schematic showing the sixth embodiment.

FIG. 19 schematically shows this embodiment. A part 7 to be inspected of an LSI circuit has leads 8 connected to wiring patterns 9 of a circuit board 6. The circuit board 6 is positioned on an X-Y table 9 and fixed thereon. A control unit 26 drives the X-Y table 19 such that the optical axis 15a of a laser beam is aligned with a central portion on the top surface of a lead 8. The laser beam emitted from a laser oscillator 12 runs along the optical axis 15a. This laser beam is first shaped into a parallel beam at a beam expander 15b and focussed by a lens 15c onto the lead to be inspected. A photomultiplier 17a is aligned with the optical axis 18a of a speckle image detection optical system, and it receives a laser beam reflected from the lead 8 through a pinhole aperture 16c displaced from an image formation position 16b of a lens 16a and converts a received light signal into an electric signal. The electric signal from the photomultiplier 17a is fed to A/D converters 44 and 45 through a low-pass filter 42 and a high-pass filter 43, respectively, so as to be converted into digital signals which are fed to a control unit 26.

Figure 20:
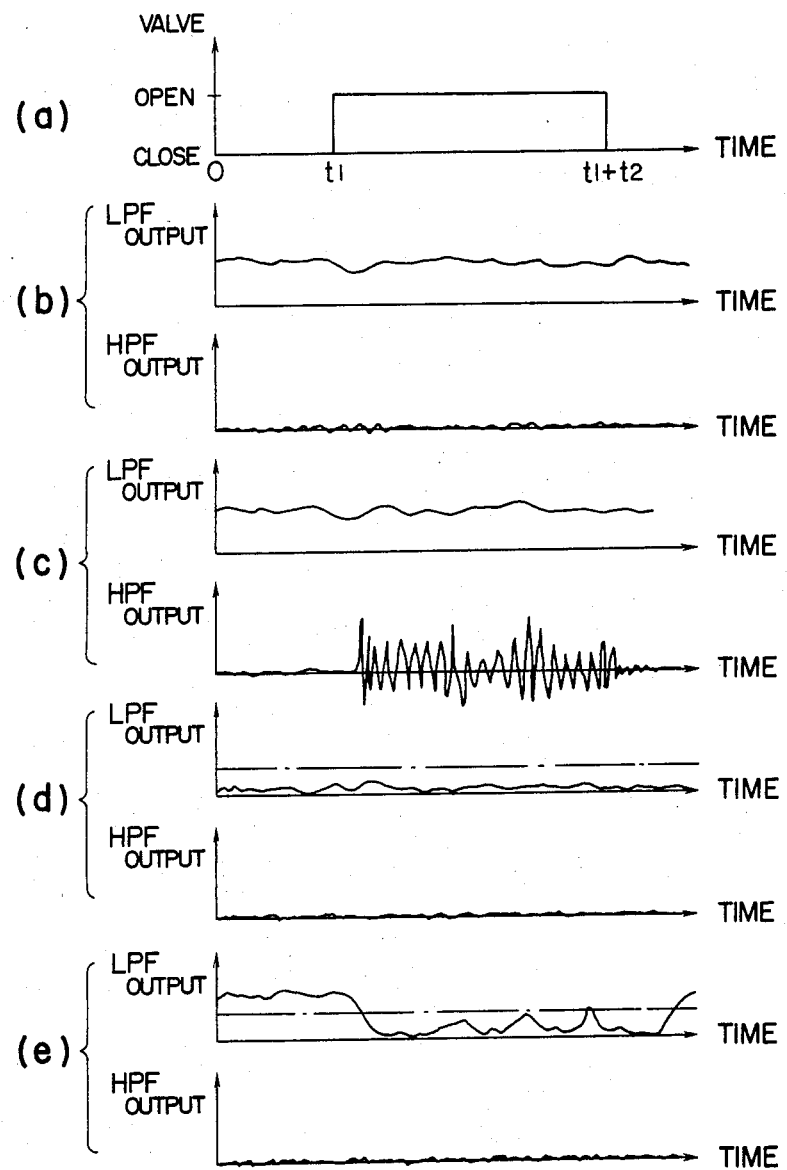
FIG. 20 is a waveform diagram showing signals detected in the sixth embodiment.

With this inspection apparatus, an operation for defect judgement is carried out as will be described with reference to FIG. 20. As shown at section (a) in FIG. 20, the control unit 26 opens a valve for $t_2$ seconds following a lapse of $t_1$ seconds from the reception by the control unit of the digital signals from the A/D converters 44 and 45. Consequently, a highly pressurized air (or gas) from a nozzle 10 is applied to a soldered portion of the lead 8. When the lead 8 is correctly soldered, both the signals passing through the low-pass filter 42 and the high-pass filter 43 will not change greatly before and after opening of the valve as shown at section (b) in FIG. 20. However, when the lead 8 is incorrectly soldered, only the signal passing through the high-pass filter 43 vibrates greatly after opening of the valve. When the lead 8 is displaced or incorrectly positioned and the correct irradiation of the laser beam on the top surface of the lead 8 is prevented, a laser speckle pattern image is formed on a dotted line shown in FIG. 19 with the result that the photomultiplier 17a receives no incident light and the output signal from the low-pass filter 42 falls below a predetermined level $V_{TH}$ as shown at section (d) in FIG. 20. However, if the application of air causes the lead 8 to displace, then the output signal from the low-pass filter 42 will fall below the predetermined level $V_{TH}$ only for a time interval ($t_1$ to $t_1 + t_2$) during which the air application is carried out, as shown at section (e) in FIG. 20.

Thus, the defect judgement by the control unit 26 will be summarized as follows:

(1) When the output signal of the low-pass filter 42 prior to the air application is equal to or less than $V_{TH}$, the presence of pseudo-defect (lead displacement) is determined.

(2) For the output signal of the low-pass filter 42 prior to the air application being larger than $V_{TH}$, (i) if the output signal of the low-pass filter 42 after the air application is equal to or less than $V_{TH}$, floating defect (defective joint) is determined, and (ii) if the output signal of the low-pass filter 42 after the air application is larger than $V_{TH}$, (a) floating defect (defective joint) is determined when the output signal of the high-pass filter 43 after the air blowing is vibratory, and (b) the acceptable joint is determined when the output signal of the high-pass filter 43 after the air application is not vibratory.

Figure 21:
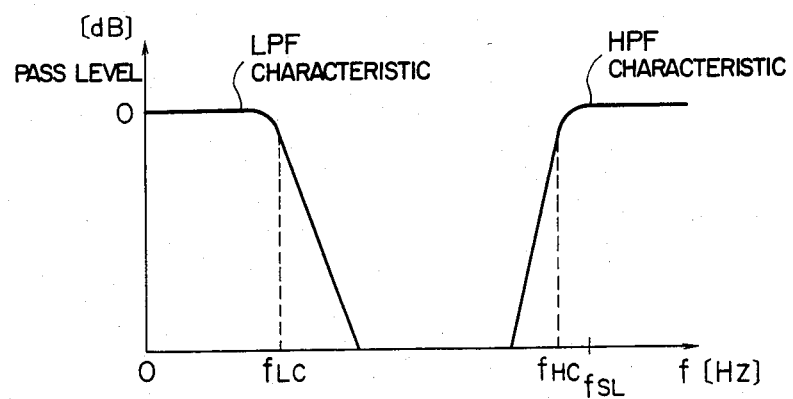
FIG. 21 is a graph illustrative of characteristics of filters used in the sixth embodiment.

The above four states are discriminated to judge the joint junction state. Results of the defect judgement may be outputted immediately or may be stored in a memory temporarily and then outputted all together. The defective lead may be marked by means of a suitable marker (not shown). After an inspection for one lead has been completed, the control unit 26 again issues to the table controller an instruction for advancing the X-Y table 19 to the next lead position. The operation for defect judgement described above is repeated until the judgement for all the leads terminates. Frequency characteristics of the high-pass filter 43 and the low-pass filter 42 are related to each other as below, $$f_{HC} < f_{SL} \tag{2}$$

$$f_{LC} < < f_{HC} \tag{3}$$

where $f_{HC}$ and $f_{LC}$ are cut-off frequencies of the filters 43 and 42, respectively, and $f_{SL}$ is a minimum value of natural frequency of a lead which floats under the application of the air application and is generally determined experimentally. The above relationship is illustrated in FIG. 21. The laser oscillator 12 used in this embodiment essentially emits an interfering light beam and may include a gas (such as He-Ne) laser, a solid state (such as ruby) laser and a semiconductor laser. The photomultiplier 17a is essentially required to have sensitivity to a wavelength of the light source and to be sufficiently sensitive to detect the laser speckle pattern image, and it may be replaced with a phototube, a phototransistor or a photodiode. Especially, with a photodiode having a small light receiving target, the pinhole aperture 16c may be dispensed with. Further, filtering of the detection signal and judgement processing may obviously be replaced by modified equivalent functions. The positional and inclination angular relationship between the laser beam irradiation optical system 15 and the speckle image detection optical system 18 may of course be reversed.

As described above, in the embodiments according to the present invention, the soldered portions of flat package type parts of the printed circuit board and wire bonding portions of the LSI circuit can be checked for their quality of joint junction states with high reliability and at high speeds in a contactless fashion, and the inspection of the junction states, which has conventionally been relied on visible inspection or viewing, can be automated. Especially, the inspection method and apparatus according to the invention are effective to inspect junction states of parts assembled at high density.

We claim:

1. An inspection apparatus for joint junction states comprising:
    vibration applying means for applying a vibration to an object to be inspected which is jointed to a board in a contactless fashion, said vibration applying means including gas jet means for injecting a gas, said gas jet means having a main jet port and control flow ports on both sides of said main jet port, flow outputs from said control flow ports being variably controlled to vibrate the direction of a main jet;
    optical means for optically detecting a vibratory state of said object vibrated by said vibration applying means; and
    analyzing means for analyzing a vibratory state of said object detected by said optical means so as to inspect a state of joint junction of said object to said board.

2. An inspection method for joint junction states comprising the steps of:
    applying a vibration in a contactless fashion to a first object jointed to a second object;
    applying a turbulence to said vibration applied to said first object;
    optically detecting a vibratory state of said first object in a contactless fashion; and
    analyzing the detected vibratory state of said first object to determine the state of the joint junction of said first object to said second object.

3. An inspection method according to claim 2, wherein the step of optically detecting the vibratory state of said first object includes converting a light beam reflected from said first object into an electrical signal, and said step of analyzing the detected vibratory state of said first object includes passing said electrical signal through a high-pass filter and passing said electrical signal through a low-pass filter, determining a floating defect of said first object when the output of said low-pass filter is not higher than a predetermined threshold level, and determining a floating defect of said first object when the output of said low-pass filter is higher than said predetermined threshold level and the output of said high-pass filter is vibratory.

4. An inspection method according to claim 2, wherein the steps of applying a vibration to said first object and applying a turbulence to said vibration applied to said first object includes providing gas jet means having a main jet port for injecting gas onto said first object and at least one control flow port on a side of said main jet port, and variably controlling a flow output from said at least one control flow port to vibrate the direction of a main jet.

5. An inspection method according to claim 4, wherein said gas jet means includes control flow ports on opposite sides of said main jet port and variably controlling the flow outputs from said control flow ports to vibrate the direction of said main jet.

6. An insepction apparatus for joint junction states comprising:
    vibration means for indirectly vibrating an object to be inspected in a contactless fashion, said vibration means including means for applying a vibration to said object and means for applying a turbulence to said vibration applied to said object;
    laser beam irradiation optical means including a laser light source, an irradiation optical system and a half mirror, for irradiating a laser beam emitted from aid laser light source onto said object;

speckle image detection optical means including a focussing optical system and a linear sensor, for detecting a laser speckle pattern image generated from said object being irradiated with said laser beam; and control means including a linear sensor drive circuit, a deffect judging unit for judging the laser speckle pattern image observed by said linear sensor, a vibration control unit for controlling said vibration means, a laser beam control unit for controlling the emission of said laser beam, and a position control unit for controlling the position of said object to be inspected.

7. An inspection apparatus according to claim 6, wherein said vibration means comprises gas jet means having a main jet port for injecting gas and at least one control flow port on a side of said main jet port, wherein a flow output from said at least one control flow port is variably controlled to vibrate the direction of a main jet.

8. An inspection apparatus according to claim 7, wherein said gas jet means includes control flow ports on opposite sides of said main jet port, wherein flow outputs from said control flow ports are variably controlled to vibrate the direction of said main jet.

9. An inspection apparatus for inspecting joint junction states comprising:

vibration applying means for applying a vibration to an object to be inspected which is jointed to a board, said vibration applying means including gas jet means having a main jet port for ejecting gas and at least one control flow port on a side of said main jet port, a flow output from said at least one control flow port being variably controlled to vibrate the direction of a main jet;

optical means for optically detecting a vibratory state of said object vibrated by said vibration applying means; and analyzing means for analyzing the vibratory state of said object detected by said optical means so as to inspect the state of the joint junction of said object to said board.

10. An inspection apparatus according to claim 9, wherein said gas jet means includes control flow ports on opposite sides of said main jet port, flow outputs from said control flow ports being variably controlled to vibrate the direction of said main jet.

11. An inspection apparatus according to claim 9 wherein said optical means comprises laser beam irradiation means for irradiating a laser beam on said object to be inspected, and a detection optical system for detecting a laser speckle pattern image generated from said object.

12. An inspection apparatus according to claim 11 wherein said detection optical system comprises a focussing optical system and a storage type linear sensor.

13. An inspection apparatus according to claim 11 wherein said detection optical system comprises a focussing optical system and a non-storage type parallel output linear sensor.

14. An inspection apparatus according to claim 11 wherein said detection optical system comprises a focussing optical system and a storage type two-dimensional sensor.

15. An inspection apparatus according to claim 11 wherein said detection optical system comprises a focussing optical system having a focussing position and a sensor, said sensor being disposed at said focussing position of said focussing optical system.

16. An inspection apparatus according to claim 11 wherein said detection optical system comprises a focussing optical system having a focussing position and a sensor, said sensor being disposed at a defocussing position of said optical system spaced from said focusing position of said focussing optical system.

17. An inspection apparatus according to claim 16 further comprising a cylindrical lens disposd before said sensor.

18. An inspection apparatus accordding to claim 11 wherein optical axes of said laser beam irradiation means and said detection optical system are non-coincident with each other.

* * * * *

UNITED STATES PATENT AND TRADEMARK OFFICE
CERTIFICATE OF CORRECTION

PATENT NO. : 4,641,527
DATED : Feb. 10, 1987
INVENTOR(S) : Hiroi et al.

It is certified that error appears in the above-identified patent and that said Letters Patent are hereby corrected as shown below:

IN THE TITLE PAGE:

Line 22, delete "Mar., 1985" and insert --Mar. 4, 1985--

Signed and Sealed this

Thirty-first Day of May, 1988

Attest:

DONALD J. QUIGG

Attesting Officer

Commissioner of Patents and Trademarks